(12) United States Patent
Kobetski et al.

(10) Patent No.: US 8,902,070 B2
(45) Date of Patent: *Dec. 2, 2014

(54) EYE CLOSURE DETECTION USING STRUCTURED ILLUMINATION

(71) Applicant: Tobii Technology AB, Danderyd (SE)

(72) Inventors: Miroslav Kobetski, Danderyd (SE); Peter Blixt, Hagersten (SE); Johnny Holmberg, Hallstahammar (SE); John Mikael Elvesjo, Stockholm (SE)

(73) Assignee: Tobii Technology AB, Danderyd (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/678,922

(22) Filed: Nov. 16, 2012

(65) Prior Publication Data

US 2013/0076885 A1    Mar. 28, 2013

Related U.S. Application Data

(62) Division of application No. 12/749,612, filed on Mar. 30, 2010, now Pat. No. 8,314,707.

(60) Provisional application No. 61/164,514, filed on Mar. 30, 2009.

(30) Foreign Application Priority Data

Mar. 30, 2009    (EP) .................................... 09156722

(51) Int. Cl.
*G08B 23/00*    (2006.01)
*H04N 7/18*    (2006.01)
(Continued)

(52) U.S. Cl.
CPC . *H04N 7/18* (2013.01); *Y02T 10/84* (2013.01); *G06K 9/2018* (2013.01);
(Continued)

(58) Field of Classification Search
CPC ....... G08B 21/06; A61B 3/113; A61B 5/1103

USPC .............. 340/575–576; 348/78; 382/100–103
See application file for complete search history.

(56) References Cited

U.S. PATENT DOCUMENTS 5,867,587 A    2/1999    Aboutalib et al.
6,163,281 A    12/2000    Torch
(Continued)

FOREIGN PATENT DOCUMENTS

EP    1 394 756    8/2002
EP    1 862 111    2/2007
(Continued)

OTHER PUBLICATIONS

Li et al. "Using Sturcture Ilumination to Enhance Video-Based EY Tracking" 2007.

*Primary Examiner* — Benjamin C Lee
*Assistant Examiner* — Adam Carlson
(74) *Attorney, Agent, or Firm* — Allen, Dyer, Doppelt, Milbrath & Gilchrist, P.A.

(57) ABSTRACT

A monitoring system and method for monitoring and/or predicting drowsiness of a driver of a vehicle or a machinery operator are provided. A set of infrared, IR, or near infrared, NIR, light sources, is arranged such that an amount of the light emitted from the light source incidents on an eye of the driver or operator. The light that impinges on the eye of the driver or operator forms a virtual image of the signal sources on the eye including the sclera and/or cornea. An image sensor obtains consecutive images capturing the reflected light, wherein each image will contain glints from at least a subset or all of the light sources. A drowsiness index can be determined based on the extracted information of the glints of the sequence of images, wherein the drowsiness index indicates a degree of drowsiness of the driver or operator.

18 Claims, 2 Drawing Sheets

(51) Int. Cl.
 *G06K 9/00* (2006.01)
 *G06K 9/20* (2006.01)
 *B60K 28/06* (2006.01)
 *G08B 21/06* (2006.01)
 *A61B 5/18* (2006.01)

(52) U.S. Cl.
 CPC .......... *G06K 9/00597* (2013.01); *B60K 28/066* (2013.01); *G08B 21/06* (2013.01); *A61B 5/18* (2013.01)
 USPC ............. 340/575; 340/576; 348/78; 382/100; 382/103

(56) References Cited

U.S. PATENT DOCUMENTS

| | | | |
|---|---|---|---|
| 7,202,793 B2 * | 4/2007 | Grace et al. | 340/576 |
| 7,401,920 B1 * | 7/2008 | Kranz et al. | 351/210 |
| 7,791,491 B2 | 9/2010 | Johns | |
| 8,314,707 B2 * | 11/2012 | Kobetski et al. | 340/575 |
| 2004/0044293 A1 | 3/2004 | Burton | |
| 2007/0080816 A1 | 4/2007 | Haque et al. | |
| 2008/0069403 A1 | 3/2008 | Breed | |
| 2008/0074618 A1 | 3/2008 | Qi | |
| 2009/0103048 A1 * | 4/2009 | Tsukiji | 351/206 |

FOREIGN PATENT DOCUMENTS

| | | |
|---|---|---|
| WO | 02/50792 | 6/2002 |
| WO | 03/039358 | 5/2003 |
| WO | 2007-016739 | 2/2007 |

* cited by examiner

EYE CLOSURE DETECTION USING STRUCTURED ILLUMINATION

FIELD OF THE INVENTION

The invention generally relates to systems and methods for monitoring and predicting driver vigilance, and, in particular, to systems and methods for monitoring and predicting drowsiness and sleep onset of, for example, vehicle drivers. Other typical applications may include monitoring the pilot of an aircraft, and in areas involving related occupations such as train drivers and operators of equipment, such as cranes and industrial machinery in general.

BACKGROUND

Impairment of alertness in vehicle operators poses a danger not only to themselves but also often to the public at large. Thousands of deaths and injuries result each year that are fatigue related. Moreover, the financial costs as a result of the injuries and deaths are prohibitive. As a result, significant efforts have been made in the area of vigilance monitoring of the operator of a vehicle to detect the decrease in attention of the operator due to drowsiness and to alert her/him.

Conventional driver vigilance monitoring techniques fall within the following broad classes: (1) image acquisition and processing of facial features such as eye and head movements; (2) image acquisition and processing of road lane maintaining capability and (3) monitoring of the physiological responses of the body while driving.

However, there are several limitations with the existing technologies. A vigilance monitoring techniques based on monitoring physiological responses of the body like EEG and ECG, are intrusive, expensive and can distract or cause annoyance to the driver. In US 2004/0044293, for example, a system for monitoring, recording and/or analysing vigilance, alertness or wakefulness and/or a stressed state of an operator of equipment or machinery in a variety of situations including situations wherein the degree of vigilance of the operator has implications for the safety or well being of the operator or other persons.

The monitoring system according to US 2004/0044293 is designed, inter alia, to provide non-invasive monitoring of a driver's physiological data including movement activity, heart activity, respiration and other physiological functions. The monitored physiological data may undergo specific analysis processing to assist in determining of the driver's state of vigilance. The system is designed to detect various states of the driver's activity and detect certain conditions of driver fatigue or relaxation state that could lead to an unsafe driving condition or conditions.

The system includes means for gathering movement data associated with the driver including a plurality of sensors such as touch sensitive mats placed in locations of the vehicle that make contact with the driver, such as the seat, steering wheel, pedal(s), seat belt or the like. Each location may include several sensors or mats to more accurately monitor movements of the driver.

A processing means may be programmed to recognize particular movement signatures or patterns of movement, driver posture or profile and to interpret these to indicate that vigilance has deteriorated or is below an acceptable threshold. The sensors or mats may include piezoelectric, electrostatic, piezo ceramic or strain gauge material.

Moreover, lane tracking methods require visible lane markings and even if present are significantly impaired by snow, rain, hail, and/or dirt existing on the road. Nighttime and misty conditions are also impairments.

Existing image processing techniques used to track eyes and head patterns to track lane maintaining capability necessarily require expensive (both cost and computational requirement-wise) hardware to operate and are highly dependent on factors such as, the relative position of the driver's head with respect to the sensors, illumination, and facial features and/or mental state of the driver, whether happy, anxious, or angry. Each of these indicators suffers from a relatively low probability of detecting drowsiness. Many of the measurements for indicating drowsiness do not adequately represent the responsiveness of the driver because of such influences as road conditions, patterns and vehicle type. Moreover, the cost for these techniques is often prohibitive. Even yet, more often than not, the existing techniques detect drowsiness when it may be too late for accident prevention purposes.

In US 2007/0080816, a vigilance monitoring system for alerting a driver of a vehicle upon detecting a state of drowsiness by calculation of a deviation between a time derivative of force and/or displacement exerted by the driver on a driver-vehicle interface, e.g., the steering wheel or the gas pedal, and a moving average for the time derivative of force and/or displacement to thereby quantify the state of drowsiness of the driver independent of conditions inside and outside the vehicle is disclosed. The system includes a sensor connected to at least one driver-vehicle interface to monitor force on and/or displacement of the driver-vehicle interface.

The system also includes an intelligent control in communication with the sensor as well as a time derivative profile modeled from the time derivative of force and/or displacement using the intelligent control. Included also is a general trend modeled from the moving average of the time derivative of force and/or displacement using the intelligent control. In addition, the system includes a spikiness index defined by a degree of deviation between the time derivative profile and the general trend to thereby quantify the state of drowsiness of the driver independent of conditions inside and outside of the vehicle. However, the system according to US 2007/0080816 may require extensive processsing capabilities in order to compute the data needed for the determination of the state of drowsiness.

In light of the problems encountered within the prior art, there is a continuing need for improved systems and methods that are capable of detecting drowsiness under different and varying conditions such as under varying light conditions, varying weather conditions and varying road conditions, for a diversity of driver physionomies and under the influence of other potentially disturbing factors such as usage of glasses etc., with a high degree of accuracy and reliability.

BRIEF SUMMARY OF THE INVENTION

Thus, an object of the present invention is to provide improved systems and methods for detecting drowsiness under different and varying conditions such as under varying light conditions, varying weather conditions and varying road conditions, for a diversity of driver physionomies and under the influence of other potentially disturbing factors such as usage of glasses etc., with a high degree of accuracy and reliability.

This and other objects of the present invention will become apparent from the specification and claims together with the appended drawings.

According to a first aspect of the present invention, there is provided a monitoring system for monitoring and/or predicting drowsiness of a driver of a vehicle or a machinery operator, the system being adapted to be arranged in the vehicle or at the machinery. The system comprises a set of infrared, IR, or near infrared, NIR, light sources, each light source being arranged in the vehicle or at the machinery such that an amount of the light emitted from the light source incidents on an eye of the driver or operator. The emitted light that impinges on the eye of the driver or operator thereby forms a virtual image of the signal source on the eye including the cornea.

An image sensor is arranged and oriented such that light reflected from the eye can be captured in an image and adapted to generate consecutive images forming a sequence of images over time, wherein each image contains glints from at least a subset or all of the light sources, an image processing unit adapted to extract information of the glints in the images by processing the images using an image processing algorithm, and a determining unit adapted to determine a drowsiness index based on the extracted information of the glints of the sequence of images, wherein the drowsiness index indicates a degree of drowsiness.

According to a second aspect of the present invention, there is provided a method for monitoring and/or predicting drowsiness of a driver of a vehicle or a machinery operator. The method includes emitting light using a set of infrared, IR, or near infrared, NIR, light sources, each light source being arranged in the vehicle or at the machinery such that an amount of the light emitted from the light source incidents on an eye of the driver or operator. The emitted light that impinges on the eye of the driver or operator thereby forms a virtual image of the signal source on the eye including the cornea.

Further, light reflected from the eye in an image is captured using an image sensor, consecutive images forming a sequence of images over time are generated, wherein each image contains glints from at least or all subset of the light sources, the images are processed to extract information of the glints, and a drowsiness index is determined based on the extracted information of the glints of the sequence of images, wherein the drowsiness index indicates a degree of drowsiness.

Eyelid closure has been shown to be a promising predicator of drowsiness and sleep onset but there have been problems with detecting the eyelid closure with a sufficient degree of accuracy and reliability, in particular, in varying conditions such as, for example, in varying light conditions, with respect to diversity of drive or operator physiognomies, with respect to usage of glasses, etc. The present invention provides systems and methods that are capable of detecting eye-lid position and eye opening/closure amplitude with a high degree of accuracy and reliability under varying conditions. The present invention is based on the insight that a structured illumination of an eye, or a cornea, of a driver of a vehicle or a machinery operator can be used to detect an eye-lid position and an amplitude of eye opening/closure with a high degree of accuracy and reliability. This information may, in turn, be used to determine a drowsiness index indicating a degree of drowsiness of the driver or operator.

In particular, the present invention is based on the idea of arranging a set of IR or NIR illuminators or sources (e.g., LEDs), e.g., an array of IR illuminators, such that at least an amount of the light emitted from each illuminator directly, or via one or more reflections on surfaces in a vehicle or of a machinery, impinges on an eye (cornea and/or sclera) of the driver or operator. Each illuminator will thereby produce a virtual image of itself on the cornea and, optionally, the sclera, and thus forms a virtual image of the illuminator on the eye of the driver or operator. The light will be reflected by the eye and the glints or reflections are captured or acquired by means of an image sensor. Thereafter, the respective reflection from each illuminator is identified by means of image processing. When the eye is wide open, the glints from all illuminators can be identified in the sensor image of the eye and, for a semi-closed eye, the eye-lid will occlude some or all of the glints, and consequently, only a sub-set of the glints from the set of illuminators can be identified in the sensor image. Based on this information regarding the identified glints, a position of the eye-lid can be determined.

In principle, the glint pattern of the sensor image functions as a measuring-rod in that depending on the number of reflections being visible/occluded at a given point of time, a measure of the closuring/opening degree of the eye can be determined and hence the eye lid position. By determining an amplitude measure corresponding to the closing/opening degree over time, for example, an eye closure pattern over time can be determined. Such an amplitude measure may correspond to:

A spatial measure, for example, a center distance between a first identified glint and a last identified glint in the glint pattern or the half value distance between the first and the last glint.

A frequency measure. After (fast) Fourier transform is the spectral width inversely proportional to the spatial width. If the glint pattern has a spatial extension of Delta_X, the spectral width will be Delta_f, where Delta_X*Delta_f=C (constant). In the frequency domain, the amplitude measure is equal to C/Delta_f.

Using wavelets, the measure of overlap of the base function is valid in both the spatial and the frequency plane. A predetermined value may be given to each overlap in the spatial and frequency plane and the amplitude measure may correspond to a sum of the overlaps that satisfies predetermined criteria.

The amplitude measures for successive images may form an amplitude curve over time corresponding to the eye movement cycles or eye lid positions over time of the driver or operator.

The drowsiness index may be based on one of or a combination of two or several of the following parameters (a)-(h) calculated from the time series of the amplitude measure (the amplitude curve over time):

a) a value of the amplitude measure during a predetermined period of time corresponding to a predetermined number of images; and/or b) a negative time derivative of the amplitude measure during the predetermined period of time and/or c) a time derivative during the predetermined period of time; and/or d) a period of time between two consecutive amplitude values of the amplitude measure; and/or e) a period of time when the amplitude measure is below a predetermined threshold during the predetermined period of time;

f) a period of time when the amplitude measure is above a predetermined threshold during the predetermined period of time; and/or g) a time derivative profile of the amplitude measure of a sub-period of the predetermined period of time; and/or h) a morphology of the amplitude measure during the predetermined period of time.

As the skilled person realizes, there are other parameters that also are conceivable. In one embodiment, the predetermined period of time corresponds to an eye lid movement cycle, i.e. a period starting when the amplitude of the eye opening reaches a local peak value and ending when the amplitude of the eye opening has reached another peak value again after a period of eye closure, which corresponds to local minimum value of a period of time when the amplitude measure is below a predetermined threshold (i.e. a blink cycle of the eye). A minimum period of time depends on the sampling rate. The number of images obtained during such a cycle will of course depend on the sampling rate of the image sensor and image processing unit.

An alert person blinks, to a large extent, with rapid, "re-wetting" blinks. The typical movement pattern of such rapid blink is that the eye is closed very rapidly and is opened somewhat slower (the total blink length, i.e. the cycle from a fully open eye to a closed eye and back again to a fully opened eye, is about 100-300 ms). For a tired person, this rate of speed will be inverted or evened out in that the closure movement and the opening movement will occur at approximately the same speed. This often occurs without an increased total length of the total blink length. An increased tiredness may also result in longer periods when the eye is closed. This is often accompanied by a much slower closure speed than the opening speed. Furthermore, an increased tiredness may also result in a higher blinking frequency and more incomplete blinks (i.e. the eye is not completely closed, which is the case in "re-wetting" blinks).

These characteristics of increased tiredness can be approximated using the calculated parameters a-h, and the drowsiness index may based on any one of or a combination of:

the relation between blinking amplitude and maximum closure speed;
blinking frequency; or
period of time during which the eye is closed—integrated over a longer period of time (PERCLOS) or as a relation between slow blinks and fast blinks.

According to an embodiment of the present invention, the set of IR light sources is an array of LEDs arranged in a straight line. However, alternative designs are also conceivable such as, for example, in a curved fashion. If the invention is implemented in vehicle, e.g., a car, an array of IR light sources may be arranged on a windscreen post arranged such that the light emitted is directed onto the eye or eyes of the driver. In an alternative design, an array of IR light sources may be arranged on the upper side of the instrument panel such that light emitted is reflected by the windscreen onto the eye or eyes of the driver. The image sensor may be arranged such that the light reflected from the eyes can be captured directly or via a further reflection on the windscreen.

According to embodiments of the present invention, the IR or NIR sources may emit modulated IR light for thereby being distinguishable from disturbing background light, for example, in a vehicle application background light from traffic signs, street lights, etc. In other words, the IR sources may transmit multiplexed signals over the IR spectrum. This facilitates identifying of the glints in the sensor image sequence generated by the image sensor. Suitable modulation schemes include modulation with respect to time, such as frequency modulation, phase-locking, pulse-width modulation and modulation by orthogonal codes. Alternatively, the IR sources are synchronised and adapted to emit signals in separate time slots of a repetitive time frame. As another alternative, optical modulation can be used, wherein the IR sources emit at a specific wavelength, such as 750 nm, 850 nm and 950 nm, and absorption filters or dielectric filters are provided at the IR sensor to separate the light emitted by the sources from other light in the environment. As yet another alternative, IR signal sources can be made distinguishable from other disturbing light sources in the environment by providing them with a specific polarization characteristic.

The image sensor can be a 1D or 2D imaging device and IR or NIR image sensor may comprise a sensor surface, which is preferably plane, and which is arranged at some known distance from an optical aperture, such as a fixed or variable diaphragm, of the image sensor. This way, all light rays incident on the sensor surface will pass essentially through a common point, namely the center of the optical aperture in the case of a pinhole camera model. In Gaussian optics, nodal points define the incident angles of the IR beams. It is further possible to detect a position of an incident light ray from a reflection from an eye on the sensor surface. The position of the reflection may be a peak-intensity point, in which the maximal intensity is received or the centroid for sub-pixel resolution.

Thus, the virtual image of the light sources on the eye, i.e. the pattern formed on the sclera and/or the cornea, which is reflected back to the image sensor, will produce a glint pattern on the sensor surface. That, is a glint image will be created. The glint image can be analysed in the spatial domain using, for example, techniques based on morphology such as connected components, techniques based on gradients such as star bursts, techniques based on energy minimizing such as active contours, or techniques based on feature detection such as mean-shift or Viola-Jones, or in the frequency domain using, for example, fast Fourier transforms, or in both using wavelet-based analysis. However, the way of obtaining information from the glint pattern is not limited to these methods.

In one embodiment of the present invention, the size of the glint pattern on the image, e.g., the length of the arrays of glints, is used to determine the distance to the eye of the driver or operator to the array of LEDs. The radius of curvature of the human eye can be approximated to r mm and may therefore be modeled as a convex mirror with a focal length: $f=r/2$. Further, if the camera is calibrated, a magnifying factor, M, is known and thereby the distance to an object (eye) can be determined from the following:

$$M=(d-f)/f$$

According to embodiments of the present invention, the drowsiness index may be used to alert the driver or operator that of an increased degree of drowsiness, for example, upon detection of that the drowsiness index has exceeded a predetermined threshold. The determining unit or a control unit controlling the drowsiness monitoring system may alert the driver or operator via an alert system. If implemented in a vehicle, the alert system may use the preexisting onboard computer of the vehicle to alert the driver using the radio, existing alarm tones and/or alarm light for the seatbelt and/or door detections system. Other alert systems such as an alarm with audible and visual displays could be included into the alert system. The alert system may also include a vibrating element for causing the seat to vibrate.

As will be apparent from this specification and claims, the present invention can be implemented in a number different applications, except from vehicles, including monitoring the pilot of an aircraft, and in areas involving related occupations such as train drivers and operators of equipment such as cranes and industrial machinery in general.

As the skilled person realizes, steps of the methods according to the present invention, as well as preferred embodiments thereof, are suitable to realize as computer program or as a computer readable medium.

These and other aspects of the invention will be apparent from and elucidated with reference to the embodiments described hereinafter. All terms used herein are to be interpreted according to their ordinary meaning in the technical field, unless explicitly defined otherwise herein.

BRIEF DESCRIPTION OF THE DRAWINGS

Embodiments of the present invention will be described with reference to the accompanying drawings, on which.

DETAILED DESCRIPTION OF EMBODIMENTS OF THE INVENTION

The present invention relates to a drowsiness monitoring system. The embodiments disclosed herein are merely exemplary or representative of the present invention. The present invention is not to be limited to the specific disclosures presented herein.

Figure 1:
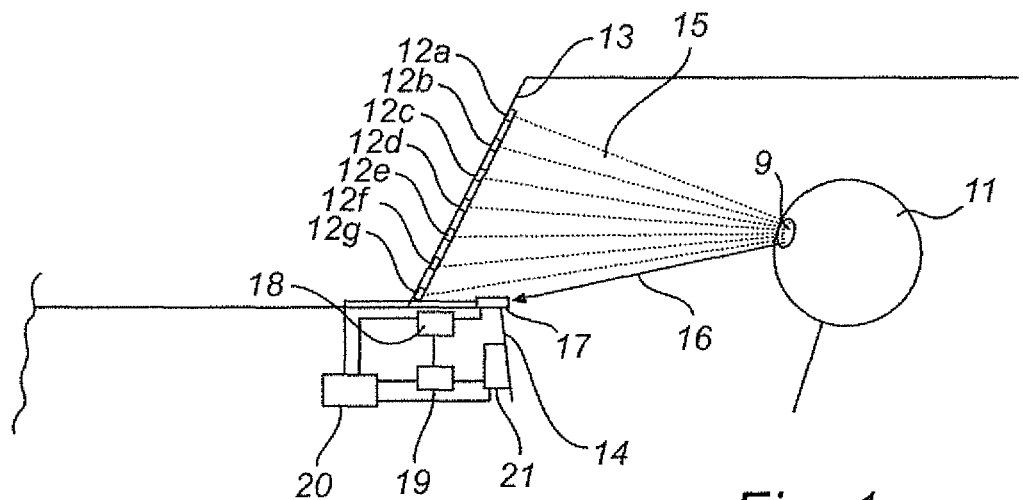
FIG. 1 is a schematic drawing of a system for monitoring drowsiness implemented in a vehicle.

With reference generally to FIGS. 1-6, embodiments of the present invention will be described. In FIG. 1, a part of a vehicle, for example, a car in which the present invention can be implemented is schematically shown in cross-section. An array or set of IR or NIR light sources 12a-12g are arranged on a windscreen post 13 of a vehicle 10. In this illustrated embodiment of the present invention, the set of light sources includes seven light sources, e.g., LEDs, 12a-12g. In connection to this, it should be pointed out that this is merely exemplifying, and the set of light sources may include, for example, five, eight or nine light sources. The higher number of light sources arranged in the set, the higher resolution of the eye lid movement is possible to achieve.

However, the resolution also depends, inter alia, on factors such as the distance between the set of light sources and the eyes of the driver, the distance between the individual light sources, the amount of emitted light that actually impinges on the eye, the amount of light reflected from the eye that is captured by the light sensor, the image processing of the images including the reflected light (i.e. the glints), etc. One key characteristic of the set of light sources 12a-12g is however that it should be arranged such that at least an amount of the emitted light impinges on the sclera and/or the cornea of the driver, which amount must be sufficiently high to be reflected by the eye such that the reflection can be captured by an image sensor.

In this embodiment, the set of light sources is arranged as an array in a straight line. Alternative designs are also conceivable such as, for example, arranging the set of light sources in a curved fashion. If implemented in vehicle, the set light sources may be arranged on the upper side of an instrument panel 14 such that light emitted is reflected by the windscreen (see FIG. 5) onto the eye or eyes (i.e. the sclera and/or the cornea) of the driver. The light sources are in this embodiment LEDs adapted to emit light in, for example, 750 nm, 850 nm or 950 nm.

In order to improve the accuracy of the drowsiness monitoring, the IR or NIR sources may emit modulated IR light for thereby being distinguishable from disturbing background light, for example, in a vehicle application background light from traffic signs, street lights, etc. In other words, the IR sources may transmit multiplexed signals over the IR spectrum. This facilitates identifying of the glints in the sensor image sequence generated by the image sensor. Suitable modulation schemes include modulation with respect to time, such as frequency modulation, pulse-width modulation and modulation by orthogonal codes.

Alternatively, the IR sources are synchronised and adapted to emit signals in separate time slots of a repetitive time frame. As another alternative, absorption filters or dielectric filters are provided at the IR sensors to remove light from other sources. A further alternative may be to provide the IR signal sources with a specific polarization characteristic.

Figure 2:
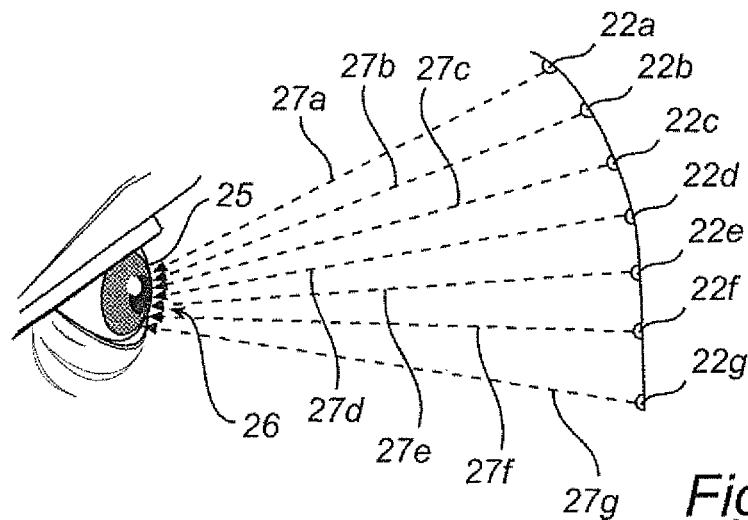
FIG. 2 is a schematic drawing illustrating principles of the present invention.
Figure 3:
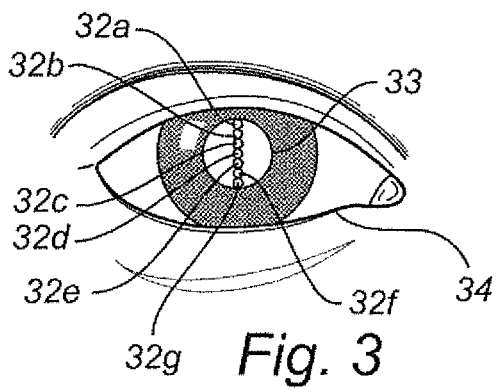
FIG. 3 is a photograph of a fully open is in which the glints from an array of LEDs can be seen.
Figure 4:
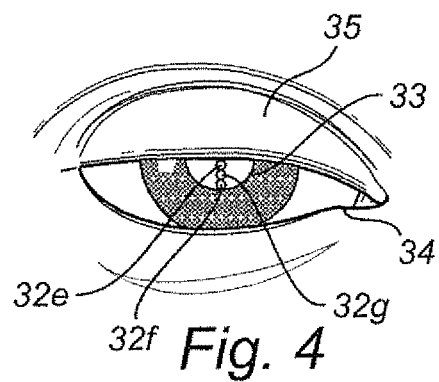
FIG. 4 is a photograph of a semi-closed eye is in which the glints from some of the LEDS of an array of LEDs can be seen.

Thus, an amount of the emitted light 15 from the respective light source 12a-12g impinges on the eye 9, i.e. on the sclera and/or the cornea, of the driver 11 and thereby produces a virtual image on the sclera and/or the cornea, see FIGS. 2-4. The light that impinges on the eye 9 thereby producing the virtual image will be reflected 16 and an image sensor 17 is positioned such that it is capable of capturing an amount of the reflected light 16. For example, the image sensor may be located on the instrument panel 14 or may be integrated in the instrument panel 14. The image sensor 17 may be a camera unit that is sensitive for IR radiation, for example, a silicon-based digital cameras having a good sensibility in the near IR spectrum.

The image sensor can be a 10 or 20 imaging device and the IR or NIR image sensor may comprise a sensor surface, which is preferably plane, and which is arranged at some known distance from an optical aperture, such as a fixed or variable diaphragm, of the image sensor. Thus, the virtual image of the light sources on the eye, i.e. the pattern formed on the sclera and/or the cornea, which is reflected back to the image sensor 17, will produce a glint pattern on the sensor surface. That is, in each snapshot a glint image will be created and over a sequence of images the glint pattern during different eye lid positions will hence be captured by the image sensor 17.

An image processing unit 18 is connected to the image sensor 17. The glint image can be analysed in the spatial domain using, for example, techniques based on morphology such as gradient edge detection techniques including Sobel, Prewitt, Robert, Canny or star burst in combination with connected components, finding zero crossing by combination of Gaussian filtering and Laplacian derivation, techniques based on energy minimizing such as active contours, or techniques based on feature detection such as mean-shift or Viola-Jones, or in the frequency domain using, for example, fast Fourier transforms, or in both using wavelet-based analysis.

However, the way of obtaining information from the glint pattern is not limited to these methods. The image processing unit 18 is thus adapted to extract information of the glints in each image by processing the images using an image processing algorithm, as discussed above. Further, a determining unit 19 is connected to the image processing unit 18 and is adapted to determine a drowsiness index based on the extracted information of the glints of a sequence of images, wherein the drowsiness index indicates a degree of drowsiness. The operation of the set of light sources 12a-12g, the image sensor 17, the image processing unit 18, and the determining unit 19 may be controlled by a control unit 20. In one embodiment, the image sensor 17, the image processing unit 18, and the determining unit 19 are integrated into the control unit 20.

In an alternative embodiment, the control unit 20 (and/or the image sensor 17, the image processing unit 18, and the determining unit 19) is integrated into an onboard computer of the vehicle or a central processing unit adapted for onboard configuration within the vehicle. The control unit 20 also includes a storage unit for storing, for example, time series data or data recorded with a time signature of the glint pattern information obtained from the image sensor 17 or time series data of the drowsiness index.

The determining unit 19 may in one embodiment be adapted to calculate or determine an amplitude measure, which may correspond to:

A spatial measure, for example, a center distance between a first identified glint and a last identified glint in the glint pattern or the half value distance between the first and the last glint.

A frequency measure. After (fast) Fourier transform is the spectral width inversely proportional to the spatial width. If the glint pattern has a spatial extension of Delta_X, the spectral width will be Delta_f, where Delta_X*Delta_f=C (constant). In the frequency domain, the amplitude measure is equal to C/Delta_f.

Using wavelets, the measure of overlap of the base function is valid in both the spatial and the frequency plane. A predetermined value may be given to each overlap in the spatial and frequency plane and the amplitude measure may correspond to a sum of the overlaps that satisfies predetermined criteria.

The amplitude measures for successive images may form an amplitude curve over time corresponding to the eye movement cycles or eye lid positions over time of the driver or operator. Generally, a high value of the amplitude measure corresponds to an eye lid position for a fully or near fully open eye and, correspondingly, when the amplitude measure has a low value it corresponds to an eye lid position for a closed or nearly closed eye.

The drowsiness index may be determined using the amplitude measure. The amplitude measure may be raw data or may be filtered using, for example, any one of the following techniques:

moving average;
Gaussian filtering;
Low-pass finite impulse response (FIR) filtering; and
Kalman filtering.

In embodiments of the present invention, the determining unit 19 is adapted to calculate one or several of the following parameters (a)-(h) using the time series of the amplitude measure, wherein:

a) a value of the amplitude measure during a predetermined period of time corresponding to a predetermined number of images; and/or
b) a negative time derivative of the amplitude measure during the predetermined period of time and/or
c) a time derivative during the predetermined period of time; and/or
d) a period of time between two consecutive amplitude values of the amplitude measure; and/or
e) a period of time when the amplitude measure is below a predetermined threshold during the predetermined period of time;
f) a period of time when the amplitude measure is above a predetermined threshold during the predetermined period of time; and/or
g) a time derivative profile of the amplitude measure of a sub-period of the predetermined period of time; and/or
h) a morphology of the amplitude measure during the predetermined period of time.

The determining unit 19 is adapted to base the drowsiness index on one of or a combination of two or several of the parameters (a)-(h). As the skilled person realizes, there are other parameters that are conceivable. In one embodiment, the predetermined period of time corresponds to an eye lid movement cycle, i.e. a period starting when the amplitude of the eye opening has a maximal value and ending when the amplitude of the eye opening has reached the maximal value again after a period of eye closure (i.e. a blink of the eye) and a minimum period of time depends on the sampling rate. The number of images obtained during such a cycle will of course depend on the sampling rate of the image sensor and image processing unit.

An alert person blinks, to a large extent, with rapid, "re-wetting" blinks. The typical movement pattern of such rapid blinks is that the eye is closed very rapidly (the eye lid moves rapidly downward to close the eye) and is opened somewhat slower (the eye lid opens somewhat slower than it closes in this case). The total blink length, i.e. the cycle from a fully open eye to a closed eye and back again to a fully opened eye, is about 100-300 ms. For a tired person, this rate of speed between the closure and the opening will be inverted or evened out in that the closure movement and the opening movement will occur at approximately the same speed. This occurs substantially without an increased total length of the total blink length. An increased tiredness may also result in longer periods during which the eye is closed. This is often accompanied by a much slower closure speed than opening speed. Furthermore, an increased tiredness may also result in a higher blinking frequency and a higher number of incomplete blinks (i.e. the eye is not completely closed, which is the case in "re-wetting" blinks).

These characteristics of increased tiredness can be approximated using, for example, one or more of the calculated parameters a-h, and the drowsiness index may based on any one of or a combination of:

the relation between blinking amplitude and maximum closure speed;
blinking frequency; or
period of time during which the eye is closed—integrated over a longer period of time (PERCLOS) or as a relation between slow blinks and fast blinks.

Further, the determining unit 19 may be adapted to alert the driver 11 or operator of an increased degree of drowsiness when the drowsiness index exceeds a predetermined drowsiness index threshold. In an embodiment of the present invention, an alert system 21 is adapted to notify the driver 11 or operator of an increased degree of drowsiness when the drowsiness index has exceeded the predetermined drowsiness index threshold. The alert system 21 may use the preexisting onboard computer of the vehicle to alert the driver using the radio, existing alarm tones and/or alarm light for the seatbelt and/or door detections system. Other alert systems 21 such as an alarm with audible and visual displays could be included into the alert system. The alert system 21 may also include a vibrating element for causing the seat to vibrate.

According to one embodiment of the present invention, the array of light sources is positioned about 70 cm from the eyes of the driver or operator and seven light sources are arranged in the array with a distance of about 10 cm between adjacent light sources (in a vertical direction). Hence, the array will have a vertical length of about 70 cm and may, for example, be mounted on the windscreen post as shown in FIG. 1. The radius of curvature of the human eye can be approximated to 8 mm and may therefore be modeled as a convex mirror with a focal length, f, of 4 mm. An object (eye) distance, d, of 70 cm is therefore de-magnified 174 times according to the following:

$$M=(d-f)/f$$

The array having a vertical length of about 70 cm therefore produces a 4 mm long glint pattern on the cornea. This is shown in FIGS. 2-4. In FIG. 2, the principle of the present invention is schematically illustrated. An array of LEDs 22a-22g is positioned or oriented such that a substantial amount of the emitted light 27a-27g from respective LED impinges on the eye 24, e.g., on the sclera 25 and/or the cornea 26 of a driver or an operator. The array of LEDs 22a-22g shown is merely exemplifying. FIG. 3 is a schematic drawing of a fully open eye where the array of seven LEDs imaged onto the cornea is illustrated. The glint pattern includes seven distinct glints 32a-32g, one for each respective LED, images onto the cornea 33 of the eye 34.

In FIG. 4, it is schematically illustrated a semi-closed eye. In this position of the eye-lid, the eye-lid 35 will occlude a part of the cornea 33, which results in that only three LEDs 32e-32f are reflected by the cornea and only these three LEDs will produce glints on the sensor image. Hence, the present invention provides a system and method that are capable of detecting eye-lid position with a high degree of accuracy and reliability under varying conditions and accordingly, which may be used to determine eye opening/closure amplitude. Accordingly, when the eye is wide open, the glints from all light sources can be identified in the sensor image of the eye and, for a semi-closed eye, the eye-lid will occlude some or all of the glints, and consequently, only a sub-set of the glints from the set of illuminators can be identified in the sensor image. Based on this information regarding the identified glints, a position of the eye-lid can be determined.

In principle, the glint pattern of the sensor image function as a measuring-rod in that depending on the number of reflections being visible/occluded at a given point of time, a measure of the closing/opening degree can be determined. By determining a measure of the closing/opening degree over time, for example, an eye closure pattern over time can be determined. A larger array of LEDs could cover the whole eye and provide a more precise and accurate measurement of eye-lid closure. Instead of increasing the linear size of the array, some LEDs could be positioned closer to the driver or operator or be positioned such that the emitted light is reflected of a concave of convex surface as will be discussed below.

Figure 5:
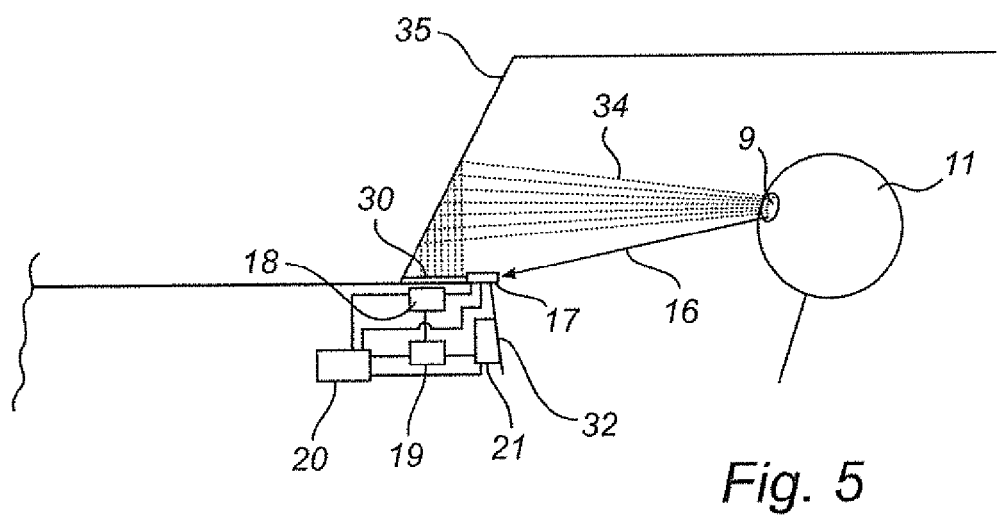
FIG. 5 is a schematic drawing of another embodiment of the system for monitoring drowsiness implemented in a vehicle.

With reference now to FIG. 5, an alternative embodiment of the present invention will be briefly discussed. Description of same or corresponding parts, units, or components having been discussed in connection to FIGS. 1 and 5 will be omitted. In this embodiment, an array of light sources 30, e.g., LEDs, is arranged on the instrument panel 32. The array of light sources 30 is positioned such that emitted light 34 will be reflected by the windscreen 35 and is further directed to impinge onto the eye 9 of the driver 11.

Figure 6:
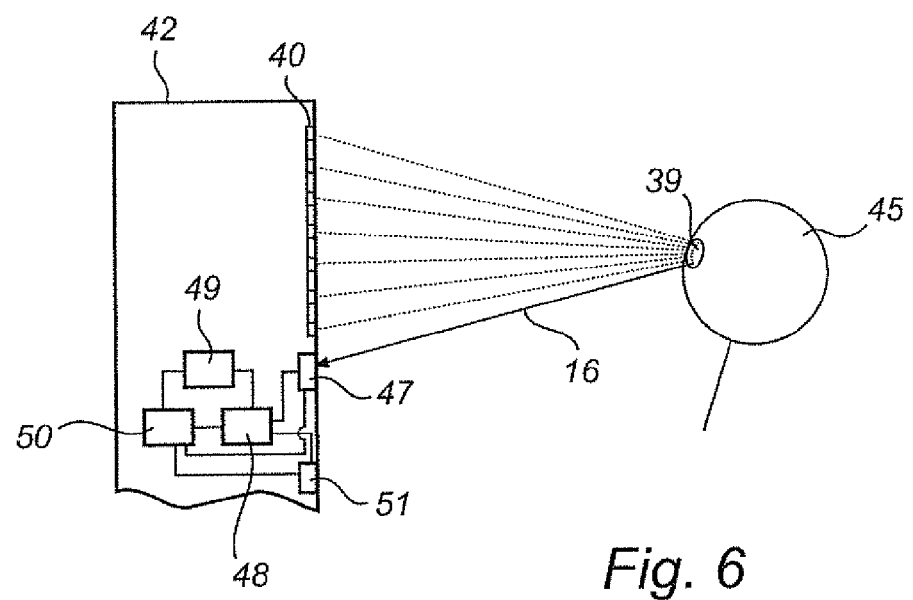
FIG. 6 is a schematic drawing of a system for monitoring drowsiness implemented in machinery equipment.

Turning now to FIG. 6, a further embodiment of the present invention will be briefly discussed. Description of same or corresponding parts, units, or components having been discussed in connection to FIGS. 1 and 5 will be omitted. In this embodiment, an array of light sources 40, e.g., LEDs, is arranged on a machinery equipment 42 and is positioned such that a substantial amount of the emitted light 44 will impinge on the eye 39 of an operator 45. The light that impinges on the eye thereby producing the virtual image will be reflected 46 and an image sensor 47 is positioned such that it is capable of capturing a substantial amount of the reflected light 46. The image sensor 47 may be of a similar type as described above. An image processing unit 48, e.g., of the type described above, is connected to the image sensor 47. Further, a determining unit 49 is connected to the image processing unit 48 and is adapted to determine a drowsiness index based on the extracted information of the glints of a sequence of images, wherein the drowsiness index indicates a degree of drowsiness in accordance with the description given above.

The operation of the array of light sources 40, the image sensor 47, the image processing unit 48, and the determining unit 49 may be controlled by a control unit 50. In one embodiment, the image sensor 47, the image processing unit 48, and the determining unit 49 are integrated into the control unit 50. In an alternative embodiment, the control unit 50 (and/or the image sensor 47, the image processing unit 48, and the determining unit 49) is integrated into a control computer of the machinery equipment 42 or a central processing unit adapted for configuration within the machinery equipment 42. The control unit 50 also includes a storage unit for storing time series data or data recorded with a time signature of the glint pattern information obtained from the image sensor 47.

Further, the determining unit 49 may be adapted to alert the operator 45 of an increased degree of drowsiness when the drowsiness index exceeds a predetermined drowsiness index threshold. In an embodiment of the present invention, an alert system 51 is adapted to notify the driver 45 or operator of an increased degree of drowsiness when the drowsiness index has exceeded the predetermined drowsiness index threshold. The alert system 51 may use the preexisting computer of the machinery to alert the operator using, for example, existing alarm tones and/or alarm light for process stop. Other alert systems 51 such as an alarm with audible and visual displays could be included into the alert system.

While the invention disclosed herein has been described by means of specific embodiments and applications thereof, numerous modifications and variations could be made therein by those skilled in the art without departing from the scope of the inventions, which is defined by the appended claims.

That which is claimed is:

1. A monitoring system for monitoring and/or predicting drowsiness of a driver of a vehicle or a machinery operator, the system being adapted to be arranged in the vehicle or at the machinery, comprising:
   a set of infrared or near infrared light sources, each light source being arranged in the vehicle or at the machinery such that a substantial amount of light emitted therefrom incidents on an eye of the driver or operator, the emitted light thereby forming an image on the eye;
   an image sensor positioned such that light reflected from the eye can be captured in an image and is adapted to generate a sequence of images over time, wherein each image contains glints from at least a subset of said light sources;
   an image processing unit adapted to extract information from the glints in the sequence of images by processing the sequence of images; and
   a determining unit adapted to
      determine an amplitude measure for at least one of the images based on the identified glints, with the amplitude measure corresponding to a degree of closing/opening of the eye over time, and
      determine a drowsiness index based on the extracted information of the glints of the sequence of images and on the amplitude measure, wherein the drowsiness index indicates a degree of drowsiness.

2. The system according to claim 1, wherein said image processing unit is adapted to identify glints in the sequence of images corresponding to reflected light from said respective light sources, wherein the extracted information includes a measure of glints being proportional to a number of glints identified in an image.

3. The system according to claim 1, wherein the amplitude measure is based on at least one of a frequency measure, a spatial measure, and a wavelet based measure.

4. The system according to claim 1, wherein said determining unit is adapted to calculate at least one of the following parameters (a)-(h):
   (a) a value of the amplitude measure during a predetermined period of time corresponding to a predetermined number of images;
   (b) negative time derivative of the amplitude measure during the predetermined period of time;
   (c) a time derivative during the predetermined period of time;
   (d) a period of time between two consecutive amplitude values Of the amplitude measure;
   (e) a period of time when the amplitude measure is below a predetermined threshold during the predetermined period of time;
   (f) a period of time when the amplitude measure is above a predetermined threshold during the predetermined period of time;
   (g) a time derivative profile of the amplitude measure of a sub-period of the predetermined period of time; and
   (h) a morphology of the amplitude measure during the predetermined period of time; and
   wherein said determining unit is adapted to base the drowsiness index on at least one of the parameters (a)-(h).

5. The system according to claim 4, wherein said determining unit is adapted to determine the drowsiness index, based on at least one of the parameters (a)-(h), to correspond to:
   a relation between a blinking amplitude and a maximum closure speed;
   a blinking frequency; and
   a period of time during which the eye is closed.

6. The system according to claim 1, wherein said determining unit is adapted to alert the driver or operator of an increased degree of drowsiness when the drowsiness index exceeds a predetermined drowsiness index threshold.

7. The system according to claim 5, further including an alert system, and wherein said determining unit is adapted to instruct said alert system to notify the driver or operator of an increased degree of drowsiness when the drowsiness index has exceeded the predetermined drowsiness index threshold, with the notification being delivered by an alert signal comprising at least one of an alert tone, an alert sound, an alert light signal, and a vibration signal.

8. The system according to claim 1, wherein the infrared or near infrared light is modulated light; and said image processing unit is adapted to discriminate reflections of the infrared or near infrared light from other light reflections captured in the images based on the modulation.

9. The system according to claim 8, wherein the modulated infrared or near infrared light is modulated with respect to at least one quantity in a group comprising time, wavelength, and polarization.

10. A method for monitoring and/or predicting drowsiness of a driver of a vehicle or a machinery operator, comprising:
   emitting light using a set of infrared or near infrared light sources, each light source being arranged in the vehicle or at the machinery such that a substantial amount of light emitted therefrom incidents on an eye of the driver or operator, the emitted light thereby forming an image on the eye;
   capturing light reflected from the eye in an image using an image sensor;
   forming a sequence of images over time, wherein each image contains glints from at least a subset of the light sources;
   processing the images to extract information from the glints;
   determining an amplitude measure for at least one of the images based on the glints, with the amplitude measure corresponding to a degree of closing/opening of the eye over time; and
   determining a drowsiness index based on the extracted information of the glints of the sequence of images and on the amplitude measure, wherein the drowsiness index indicates a degree of drowsiness.

11. The method according to claim 10, further comprising identifying the glints in the image corresponding to reflected light from respective light sources, wherein the extracted information includes a measure of glints being proportional to a number of glints identified in an image.

12. The method according to claim 10, wherein the amplitude measure is based on at least one of a frequency measure; a spatial measure, and a wavelet based measure.

13. The method according to claim 10, further comprising calculating at least one of the following parameters (a)-(h):
   (a) a maximum value of the amplitude measure during a predetermined period of time corresponding to a predetermined number of images;
   (b) a maximum negative time derivative of the amplitude measure during the predetermined period of time;
   (c) a maximum time derivative during the predetermined period of time;
   (d) a period of time between two consecutive maximum amplitude values of the amplitude measure;
   (e) a period of time when the amplitude measure is below a predetermined threshold during the predetermined period of time;
   (f) a period of time when the amplitude measure is above a predetermined threshold during the predetermined period of time;
   (g) a time derivative profile of the amplitude measure of a sub-period of the predetermined period of time;
   (h) a morphology of the amplitude measure during the predetermined period of time; and
   determining the drowsiness index based on one of or a combination of two or several of the parameters (a)-(h).

14. The method according to claim 13, further comprising determining the drowsiness index, based on at least one of the parameters (a)-(h), to correspond to:
   a relation between a blinking amplitude and a maximum closure speed;
   a blinking frequency; and
   a period of time during which the eye is closed.

15. The method according to claim 10, further comprising alerting the driver or operator of an increased degree of drowsiness when the drowsiness index exceeds a predetermined drowsiness index threshold.

16. The method according to claim 15, further comprising: notifying the driver or operator of an increased degree of drowsiness when the drowsiness index has exceeded the predetermined drowsiness index threshold, with the notification being delivered by an alert signal comprising at least one of an alert tone, an alert sound, an alert light signal, and a vibration signal.

17. The method according to claim 10, further comprising:
modulating the light emitted from the light sources; and
discriminating reflections of the infrared or near infrared light from other light reflections captured in the images based on the modulation.

18. The method according to claim 17, wherein the modulated infrared or near infrared light is modulated with respect to at least one quantity in a group comprising time, wavelength, and polarization.

* * * * *

UNITED STATES PATENT AND TRADEMARK OFFICE
CERTIFICATE OF CORRECTION

PATENT NO. : 8,902,070 B2 Page 1 of 1
APPLICATION NO. : 13/678922
DATED : December 2, 2014
INVENTOR(S) : Kobetski et al.

It is certified that error appears in the above-identified patent and that said Letters Patent is hereby corrected as shown below:

In the Specification

| | |
|---|---|
| | Delete: "10 or 20" |
| Column 8, Line 31 | Insert: -- 1D or 2D -- |

In the Claims

| | |
|---|---|
| | Delete: "Of" |
| Column 13, Line 20, Claim 4 | Insert: -- of -- |

Signed and Sealed this
Fourteenth Day of April, 2015

Michelle K. Lee
*Director of the United States Patent and Trademark Office*